US007485758B2

(12) United States Patent
Nelson et al.

(10) Patent No.: US 7,485,758 B2
(45) Date of Patent: Feb. 3, 2009

(54) METHOD FOR THE PRODUCTION OF PHENOL AND ACETONE

(75) Inventors: Mark Nelson, Mount Vernon, IN (US); Willem Lodewyk Sederel, Kalmhout (BE); Arkady Samuilovich Dyckman, Saint Petersburg (RU); Ilya Nikolaevich Grebenshchikov, Saint Petersburg (RU); Viktor Vladimirovich Pinson, Saint Petersburg (RU); Andrey Vladimirovich Zinenkov, Saint Petersburg (RU)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 11/861,381

(22) Filed: Sep. 26, 2007

(65) Prior Publication Data

US 2008/0214873 A1 Sep. 4, 2008

(30) Foreign Application Priority Data

Mar. 1, 2007 (RU) ............................... 2007108708

(51) Int. Cl.
*C07C 45/00* (2006.01)
*C07C 37/08* (2006.01)
(52) U.S. Cl. .................... 568/385; 568/768; 568/798
(58) Field of Classification Search .............. 568/385, 568/798
See application file for complete search history.

(56) References Cited

U.S. PATENT DOCUMENTS

| 3,271,457 | A | * | 9/1966 | Bewley et al. ............... 568/385 |
| 4,246,203 | A | * | 1/1981 | Wirth .......................... 568/385 |
| 6,057,483 | A |   | 5/2000 | Zakoshansky et al. |
| 7,109,385 | B2 | * | 9/2006 | Tatake et al. ................ 568/798 |
| 2005/0222466 | A1 |   | 10/2005 | Tatake et al. |

FOREIGN PATENT DOCUMENTS

| RU | 2068404 C1 | 10/1996 |
| RU | 2121477 C1 | 11/1998 |
| RU | 2291852 C1 | 1/2007 |

OTHER PUBLICATIONS

PCT International Search Report for International Application No. PCT/US2008/055808.
PCT International Search Report for International Application No. PCT/US2008/055810.
Zakoshansky, V.M. Scientific Publication, Conference Materials, Development Prospects for Chemical Processing of Fossil Fuel, "Cumene Process of Phenol-Acetone Production—History and Evolution", Khimizdata, St. Petersburg, RU pp. 25-39.
Zakoshansky, V.M. "Direction For the Development of Phenolic Process—Safety, Selectivity and Quality of the Products: I. Cumene Oxidation into Cumene Hydroperoxide (CHP)", ISBN 5-901065-94-8. Process of Oil Refining and Petrochemistry. SP6., 2005. pp. 89-107.
Zakoshansky, V.M. "Direction For Phenol Process Development—Security, Selectivity Quality and Marketable Product: II. Decomposition of Technical Cumyl Hydroperioxide". ISBN 5-901065-94-8. Process of Oil Refining and Petrochemistry, SP6., 2005. pp. 108-130.
Vasileva, I.I. and Zakoshansky, V.M. "Direction of Development Phenolic Process—Safety, Selectivity and Quality of the Commodity Products: III. Technologies of Separation and Quality of Products". ISBN 5-901065-94-8. Process of Oil Refining and Petrochemistry. SP6., 2005. pp. 131-154.
Kirk-Othmer Encyclopedia of Chemical Technology. Fourth Edition, vol. 18. Phenol. pp. 592-602.

* cited by examiner

*Primary Examiner*—Sikarl A Witherspoon

(57) ABSTRACT

A method for the production of phenol and acetone from a cumene hydroperoxide mixture comprises a first stage and a second stage and at least two serially connected reactors, wherein the first stage comprises decomposition of a cumene hydroperoxide mixture in the presence of a catalyst mixture to form a dicumyl peroxide mixture, and the second stage comprises formation of a phenol and acetone mixture from decomposition of the dicumyl peroxide mixture formed in the first stage, wherein, the first stage further comprises: a) forming a catalyst mixture by combining sulfuric acid and phenol in a weight ratio of from 2:1 to 1:1000 in a catalyst formation reactor, b) holding the catalyst mixture in the catalyst formation reactor at a temperature of about 20 to 80° C. for about 1 to 600 minutes; and, c) adding the catalyst mixture to the cumene hydroperoxide mixture to form the phenol and acetone mixture. The proposed method permits a significant reduction in the yield of hydroxyacetone that causes deterioration in the quality of commercial phenol.

19 Claims, No Drawings

METHOD FOR THE PRODUCTION OF PHENOL AND ACETONE

CROSS REFERENCE TO RELATED APPLICATIONS

This application is related to the patent application entitled "METHOD FOR THE PRODUCTION OF PHENOL AND ACETONE," concurrently filed Ser. No. 11/861,374, which claims priority from Russian Application Serial No. 2007108707). This disclosure is hereby fully incorporated herein by reference.

BACKGROUND

The present invention relates to industrial organic synthesis, specifically to production of phenol and acetone by the cumene method.

A well-known method for the production of phenol and acetone by oxidation of cumene with atmospheric oxygen, followed by the acid-catalytic decomposition of cumene hydroperoxide permits both end products to be produced with high yield (see, for example, Kruzhalov B. D., Golovanenko B. N., *Combined Production of Phenol and Acetone*, Moscow, Goskhimizdat, 1964, or Kirk-Othmer Encyclopedia of Industrial Chemistry). The method is widely used to produce these products, and is the principal technique used in world practice.

Methods are known for producing phenol and acetone in which, to reduce the yield of phenol tar, cumene oxidation products containing cumene hydroperoxide (CHP), cumene, and dimethylphenylcarbinol (DMPC) cleavage process in the presence of sulfuric acid. In the first stage, at a temperature of 55 to 80° C., most of the CHP (97 to 99%) is decomposed and dicumyl peroxide (DCP) is synthesized from DMPC and CHP. In the second stage, acetone is added at a temperature from 80 to 146° C. to the obtained reaction mixture containing phenol, acetone, dimethylphenylcarbinol (DMPC) and dicumyl peroxide (DCP). The addition is made in an amount of 1.5 to 1.8 times the original concentration of acetone. Water is also added. In some cases the acid is partially neutralized with ammonia before the second separation stage in order to ensure optimal acidity of the catalyst. Breakdown of DCP formed in the first stage, decomposition of the remaining CHP and dehydration of the remaining DMPC occur here at a temperature from 80 to 146° C. (See, for example, Russian Patent Nos. 2068404, 2121477, 2142932.)

These methods significantly reduce the amount of formed byproducts in comparison with decomposition in one stage (the yield of tar is 25 kg/t of phenol), whereas the amount of formed byproduct (hydroxyacetone) remains at a high level (and sometimes increases).

Hydroxyacetone is a precursor to 2-methylbenzofuran, which is difficult to separate from phenol and which causes a deterioration in the color indices of the commercial phenol. Elimination of hydroxyacetone from phenol by alkaline treatment complicates the process (Vasil'eva I. I., Zakoshanski V. M., *Petroleum Processing and Petrochemistry*, St. Petersburg, "Giord", 2005, page 344).

The yield of hydroxyacetone during decomposition of CHP to phenol and acetone is reduced by running the reaction in excess phenol. (See, for example, Russian Patent No. 2291852 and U.S. Pat. No. 7,109,385.) However, these methods propose that part of the commercial product (phenol) that has already passed through all separation stages be returned to the CHP decomposition stage, which undoubtedly leads to a reduction in the output of the unit because of an increase in the load on the phenol separation and purification system.

The method closest to the proposed method for the decomposition of CHP is a decomposition method that is accomplished in two stages. (See, for example, Russian Patent No. 2142932.) The prior art process is run in three serially connected mixing reactors in the first stage and in a displacement reactor in the second stage. In the first stage, CHP decomposition is carried out under conditions that are close to isothermal at a temperature of 47 to 50° C. and a catalyst concentration (sulfuric acid) of 0.018 to 0.20 wt. % by additional dilution of the reaction mass with acetone in an amount equal to 5 to 8 wt. % relative to the amount of supplied CHP. Almost all the CHP reacts, and DCP is formed from part of the CHP and DMPC.

In the second stage, the process is run while sulfuric acid is partially neutralized with ammonia to form ammonium hydrosulfate at a temperature of 120 to 146° C. A certain amount of water is added, as needed. The concentration of sulfuric acid is 0.09 to 0.10 wt. %. Decomposition of CHP and DCP occurs in a reaction medium containing phenol and acetone. These are formed from CHP and the additionally introduced acetone.

Shortcomings of the prior art method include the significant amount of hydroxyacetone in the obtained phenol. According to the inventors, this amount constitutes 1300 ppm in the reaction mass resulting from the decomposition of CHP, which significantly reduces the quality of the compound (as described in a report of the inventor of the prior art method at the conference "Outlook for Development of Chemical Processing of Fossil Fuels", KHPGI-2006, 12-15 Sep. 2006, Saint Petersburg; "Khimizdat", Saint Petersburg, 2006, page 130). Another shortcoming is the need for the partial neutralization of sulfuric acid with ammonia, which complicates the process and process control.

SUMMARY OF THE INVENTION

In an embodiment, a method for the production of phenol and acetone from a cumene hydroperoxide comprises: a first stage and a second stage and at least two serially connected reactors, wherein the first stage comprises decomposition of a cumene hydroperoxide in the presence of a catalyst mixture to form phenol, acetone, and dicumyl peroxide mixture, and the second stage comprises formation of a phenol and acetone mixture from decomposition of the remainder of cumene hydroperoxide and dicumyl peroxide formed in the first stage, wherein the first stage further comprises: a) forming a catalyst mixture by combining sulfuric acid and phenol in a weight ratio of from 2:1 to 1:1000 in a catalyst formation reactor, b) holding the catalyst mixture in the catalyst formation reactor at a temperature of about 20 to 80° C. for about 1 to 600 minutes; and, c) adding the catalyst mixture to the cumene hydroperoxide mixture to form the phenol and acetone mixture.

DETAILED DESCRIPTION OF THE INVENTION

In order to reduce the yield of hydroxyacetone (HA) during decomposition of CHP, decomposition of technical CHP is accomplished in the presence of a catalyst prepared in a separate reactor immediately before the catalyst is introduced into the CHP decomposition reactor. The catalyst is prepared by mixing phenol with sulfuric acid at a temperature from 20 to 80° C. and a sulfuric acid/phenol weight ratio of 2:1 to 1:1000, and this mixture is kept at this temperature for 1 to 600 minutes. The sulfuric acid concentration in the medium of reaction products is about 0.002 to 0.015 wt. %. The sulfuric acid used in the proposed process has a concentration of at least 75%, an in some embodiments, fuming sulfuric acid (oleum) is used as the sulfonating acid.

In an embodiment, a method for the production of phenol and acetone from a cumene hydroperoxide mixture comprises: a first stage and a second stage and at least two serially connected reactors, wherein the first stage comprises decomposition of a cumene hydroperoxide in the presence of a catalyst mixture to form phenol, acetone, and dicumyl peroxide mixture, and the second stage comprises formation of a phenol and acetone mixture from decomposition of the remainder of the cumene hydroperoxide and dicumyl peroxide formed in the first stage, wherein, the first stage further comprises: a) forming a catalyst mixture by combining sulfuric acid and phenol in a weight ratio of from 2:1 to 1:1000 in a catalyst formation reactor, b) holding the catalyst mixture in the catalyst formation reactor at a temperature of about 20 to 80° C. for about 1 to 600 minutes; and, c) adding the catalyst mixture to the cumene hydroperoxide mixture to form the phenol and acetone mixture. In an embodiment, the sulfuric acid is an aqueous sulfuric acid solution comprising at least 75 wt. % sulfuric acid. In another embodiment, the sulfuric acid is fuming sulfuric acid (oleum). In an embodiment, water is added in the second stage in an amount of up to 1% of the reaction mass. In another embodiment, the reaction temperature of the first stage is between 40 and 75° C., and in another embodiment, the reaction temperature of the second stage is between 90 and 140° C.

In an embodiment, the phenol and acetone mixture formed has a reduced level of hydroxyacetone as compared to a phenol and acetone mixture formed using a catalyst that is only sulfuric acid. In another embodiment, the catalyst mixture in step b) is held at a temperature of from about 35 to 45° C. In another embodiment, the reaction time in step b) is from about 60 to about 300 minutes.

In another embodiment, a method for the production of phenol and acetone from a cumene hydroperoxide mixture comprises: a first stage and a second stage and at least two serially connected reactors, wherein the first stage comprises decomposition of a cumene hydroperoxide in the presence of a catalyst mixture to form phenol, acetone, and dicumyl peroxide mixture, and the second stage comprises formation of a phenol and acetone mixture from decomposition of the remainder of the cumene hydroperoxide and dicumyl peroxide formed in the first stage, wherein, the first stage further comprises: a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid; b) holding the catalyst mixture in the catalyst formation reactor at a temperature of about 20 to 80° C. for about 1 to 600 minutes; and c) adding the catalyst mixture to the cumene hydroperoxide mixture to form the phenol and acetone mixture.

In another embodiment, a method for the production of phenol and acetone from a cumene hydroperoxide mixture comprises: a first stage and a second stage and at least two serially connected reactors, wherein the first stage comprises decomposition of a cumene hydroperoxide in the presence of a catalyst mixture to form phenol, acetone, and dicumyl peroxide mixture, and the second stage comprises formation of a phenol and acetone mixture from decomposition of the remainder of the cumene hydroperoxide and dicumyl peroxide formed in the first stage, wherein, the first stage further comprises: a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid; b) holding the catalyst mixture in the catalyst formation reactor at a temperature of about 35 to 45° C. for about 60 to 300 minutes; and c) adding the catalyst mixture to the cumene hydroperoxide mixture to form the phenol and acetone mixture, wherein the phenol and acetone mixture formed has a reduced level of hydroxyacetone as compared to a phenol and acetone mixture formed using a catalyst that is only sulfuric acid.

The process is run in two stages in no less than two serially connected reactors. In the first stage, decomposition of technical CHP is carried out at a temperature of from 40 to 75° C. in the presence of the aforementioned catalyst while the reaction mass is circulated in the first reactors. The catalyst concentration depends on the temperature in the reactor, the phenol/acetone ratio, the water content and the DMPC content in the feedstock. The feed rate should not exceed 10% of the circulation rate of the reaction mass (preferably less than 5%), and the circulation factor (ratio of feed rate of circulating mass to flow rate of the supplied feedstock, i.e., technical CHP) is greater than 9. Under the indicated conditions, CHP decomposes to form phenol and acetone and to synthesize DCP from CHP and DMPC at a CHP conversion rate of about 95 to 99.8%.

The synthesized DCP and the remaining CHP are decomposed in the second stage in the last reactor at a temperature of from 90 to 140° C. In contrast to the prior art method, there is no need for partial neutralization of the catalyst, since a significantly lower concentration is used in the first stage of the process. This simplifies the equipment used for the decomposition of CHP.

To control the DCP decomposition process, additional water can be required to be present in the reaction mass in an amount up to about 1% of the reaction mass. The amount of this water depends on the content of DMPC in the technical CHP, since the amount of reaction water released by the dehydration of DMPC depends on the content of DMPC in the technical CHP.

Dilution of reaction mass during acid-catalyzed decomposition of CHP, for example, with acetone, reduces the yield of α-methylstyrene (AMS) condensation products, i.e., dimers and cumylphenol.

Under these process conditions, the use of technical CHP having a similar composition reduces the yield of hydroxyacetone (HA) by a factor of about 1.5 to 2, which improves the quality of the commercial phenol when the same purification system is used. For example, the HA is reduced from about 0.12% in the comparative example to about 0.06 to 0.09% in the examples. Moreover, the reduction in the amount of employed sulfuric acid leads to a reduction in the consumption of alkali used to neutralize the acid, which ultimately reduces the amount of mineral wastes of the production process, especially sodium sulfate.

In some embodiments, to maintain the assigned temperature in the reactors, the heat released during the decomposition of CHP is taken off with heat exchangers, preferably built into the reactors.

The invention is illustrated by the following non-limiting examples.

EXAMPLES

Example 1

Decomposition of cumene hydroperoxide was carried out on a pilot unit consisting of two reactors: the first stage was a CHP decomposition reactor that had a volume of 12 mL and was equipped with a circulation loop, and the second stage reactor was a displacement reactor that had a volume of 7 mL. The reaction mass from the first stage reactor was partially fed to the second reactor and partially returned to the input of the first reactor, thus accomplishing its circulation. Catalyst and feedstock, the composition of which is shown in Table 1, were fed to the stream of reaction mass at the input to the first stage reactor. The catalyst was prepared by mixing concentrated sulfuric acid with phenol, which were fed by two pumps into a constant-temperature reactor with a capacity of 10 µL, from which the mixture was directed to the CHP decomposition reactor.

TABLE 1

Feedstock used for decomposition of CHP

| | Component | Content, wt. % |
|---|---|---|
| 1 | Cumene hydroperoxide (CHP) | 82.30 |
| 2 | Cumene | 10.32 |
| 3 | Dimethylphenylcarbinol (DMPC) | 5.27 |
| 4 | Acetophenone | 1.03 |
| 5 | Water | 0.2 |
| 6 | Dicumyl peroxide (DCP) | 0.30 |
| 7 | Phenol | 0.02 |
| 8 | Unidentified | 0.56 |

The feedstock having the composition shown in Table 1, as well as a catalyst obtained directly by mixing concentrated sulfuric acid at a rate of 1 µL/h and phenol at a rate of 9 µL/h (ratio 1:5), were fed to the CHP decomposition reactor, and the mixture was kept for 60 minutes at a temperature of 50° C. As used herein, concentrated sulfuric acid means "commercially available usual sulfuric acid", which generally means about 93 to 96% sulfuric acid ($H_2SO_4$). This feed corresponds to a sulfuric acid concentration of 0.007 wt. % in the reaction medium. The rate of circulation of the reaction mass was 500 mL/h. The temperature in the reactor was kept at a level of 40° C. by supplying a heat transfer agent of the corresponding temperature to the jacket of the reactor.

The stream emerging from the first stage reactor was diluted with acetone supplied at a rate of 8 mL/h, and was fed to the second stage reactor heated to a temperature of 125° C. The stream emerging from the second stage reactor was cooled and analyzed by GC. The composition of the reaction mass of CHP decomposition is shown in Table 2.

TABLE 2

Composition of reaction mass of CHP decomposition

| Component | Concentration, wt. % |
|---|---|
| Phenol | 40.69 |
| Acetone | 41.89 |
| Dicumyl peroxide (DCP) | 0.28 |
| Dimethylphenylcarbinol (DMPC) | 0.14 |
| Cumyl phenols | 0.37 |
| Sum of α-methylstyrene dimers | 0.17 |
| Acetophenone | 1.10 |
| α-Methylstyrene (AMS) | 2.98 |
| Cumene | 10.72 |
| Hydroxyacetone (HA) | 0.07 |
| Mesityl oxide | 0.001 |
| Unidentified | 0.67 |
| Water | 0.92 |

Example 2

Decomposition of CHP was carried out in the same equipment as in Example 1, and a mixture having the composition shown in Table 3 was used as feedstock.

The feedstock was supplied to the reactor at a rate of 10 mL/h, and concentrated (~96%) sulfuric acid was fed at a rate of 0.55 µL/h, which corresponded to a concentration of 0.009 wt. %, and phenol for mixing with sulfuric was supplied at a rate of 0.45 µL/h, which corresponded to a sulfuric acid/phenol ratio of 2:1. The mixture of phenol and sulfuric acid was held for 600 minutes at a temperature of 20° C. The circulation rate of the reaction mass was 200 mL/h. The reaction mass emerging from the first stage reactor was mixed with acetone supplied at a rate of 3 mL/h, and was fed to the second stage reactor. The temperature was 50° C. in the first stage reactor, and 140° C. in the second stage reactor. Table 4 shows the composition of the reaction mass resulting from the CHP decomposition.

Example 3

Decomposition of CHP was carried out in the same equipment and under the same conditions as in Example 2, except that 0.3 µL/h of 30% fuming sulfuric acid (oleum) was fed to the reactor, and phenol was fed at a rate of 600 µL/h (the ratio in terms of sulfuric acid to phenol in this Example was 1:1000) to prepare the catalyst. The residence time of the mixture in the reactor was 1 minute at a temperature of 80° C. Table 4 shows the composition of the reaction mass resulting from the CHP decomposition.

Example 4

Decomposition of CHP was carried out in the same equipment and under the same conditions as in Example 1, but 75% sulfuric acid was supplied to the reactor at a rate of 2 µL/h, and phenol was supplied at a rate of 5 µL/h (the ratio in terms of sulfuric acid to phenol was 1:2). The residence time of the mixture in the reactor was about 80 minutes at a temperature of 60° C. The composition of the reaction mass is shown in Table 4.

TABLE 3

Feedstock used for decomposition of CHP

| | Component | Content, wt. % |
|---|---|---|
| 1 | Cumene hydroperoxide (CHP) | 80.46 |
| 2 | Cumene | 12.31 |
| 3 | Dimethylphenylcarbinol (DMPC) | 5.31 |
| 4 | Acetophenone | 0.54 |
| 5 | Water | 0.1 |
| 6 | Dicumyl peroxide (DCP) | 0.61 |
| 7 | Phenol | 0.46 |
| 8 | Unidentified | 0.21 |

TABLE 4

Composition of reaction mass of CHP decomposition in Examples 2 to 4

| | Concentration, wt. % | | |
|---|---|---|---|
| Component | Example 2 | Example 3 | Example 4 |
| Phenol | 40.88 | 43.60 | 40.67 |
| Acetone | 44.61 | 42.62 | 44.62 |
| Dicumyl peroxide (DCP) | 0.02 | 0.04 | 0.09 |

TABLE 4-continued

Composition of reaction mass of CHP decomposition in Examples 2 to 4

| Component | Concentration, wt. % | | |
|---|---|---|---|
| | Example 2 | Example 3 | Example 4 |
| Dimethylphenylcarbinol (DMPC) | 0.06 | 0.05 | 0.10 |
| Cumyl phenols | 0.16 | 0.13 | 0.18 |
| Sum of α-methylstyrene dimers | 0.07 | 0.05 | 0.10 |
| Acetophenone | 0.51 | 0.48 | 0.54 |
| α-Methylstyrene (AMS) | 2.50 | 2.43 | 2.46 |
| Cumene | 10.21 | 9.59 | 10.14 |
| Hydroxyacetone (HA) | 0.06 | 0.05 | 0.09 |
| Mesityl oxide | 0.01 | 0.01 | 0.01 |
| Unidentified | 0.27 | 0.32 | 0.29 |
| Water | 0.66 | 0.64 | 0.70 |

Example 5

Decomposition of CHP was carried out in the same equipment as in Example 1, except that a mixture having the composition shown in Table 5 was used as feedstock.

The feedstock was fed to the reactor at a rate of 25 mL/h, concentrated (96%) sulfuric acid was fed at a rate of 1.3 μL/h, which corresponded to a concentration of 0.009 wt. %, and phenol for mixing with sulfuric acid was fed at a rate of 3.4 μL/h, (which corresponded to a sulfuric acid/phenol ratio of 1:1.5). The mixture of phenol and sulfuric acid were held for 140 minutes at a temperature of 42° C. The circulation rate of the reaction mass was 200 mL/h. The reaction mass emerging from the first stage reactor was mixed with acetone fed at a rate of 11 mL/h, and water fed at a rate of 0.2 mL/h. The obtained mixture was fed to the second stage reactor. The temperature was 40° C. in the first stage reactor, and 90° C. in the second stage reactor. The composition of the reaction mass resulting from the CHP decomposition is shown in Table 6.

TABLE 5

Feedstock used for CHP decomposition

| | Component | Content, wt. % |
|---|---|---|
| 1 | Cumene hydroperoxide (CHP) | 82.73 |
| 2 | Cumene | 11.92 |
| 3 | Dimethylphenylcarbinol (DMPC) | 3.82 |
| 4 | Acetophenone | 0.52 |
| 5 | Water | 0.06 |
| 6 | Dicumyl peroxide (DCP) | 0.64 |
| 7 | Phenol | 0.02 |
| 8 | Unidentified | 0.29 |

TABLE 6

Composition of reaction mass of CHP decomposition in Example 5

| Component | Concentration, wt. % |
|---|---|
| Phenol | 43.28 |
| Acetone | 42.80 |
| Dicumyl peroxide (DCP) | 0.03 |
| Dimethylphenylcarbinol (DMPC) | 0.08 |
| Cumyl phenols | 0.21 |
| Sum of α-methylstyrene dimers | 0.11 |
| Acetophenone | 0.47 |
| α-Methylstyrene (AMS) | 2.23 |
| Cumene | 8.87 |
| Hydroxyacetone (HA) | 0.05 |

TABLE 6-continued

Composition of reaction mass of CHP decomposition in Example 5

| Component | Concentration, wt. % |
|---|---|
| Mesityl oxide | 0.01 |
| Unidentified | 0.92 |
| Water | 0.94 |

Example 6 (Comparative Example)

The CHP cleavage reaction was carried out using the same equipment as in Example 1, but the feed of composition presented in Table 7 was used. CHP feed was pumped at rate of 26 ml/hr, and the sulfuric acid rate was 4 μL/h. Circulation rate and temperature regime used were the same as presented in Example 1.

TABLE 7

CHP cleavage feed

| | Component | Concentration, wt. %. |
|---|---|---|
| 1 | Cumene hydroperoxide (CHP) | 77.41 |
| 2 | Cumene | 11.77 |
| 3 | Dimethylbenzyl alcohol (DMBA) | 4.21 |
| 4 | Acetophenone | 0.53 |
| 5 | Water | 0.5 |
| 6 | Dicumylperoxide (DCP) | 0.46 |
| 7 | Acetone | 4.99 |
| 8 | Unknowns | 0.15 |

Reaction product discharged form the first stage reactor was passed to the second stage reactor together with a 5% ammonia solution in water fed at rate of 8 μL/h. The composition of reaction mixture produced is presented in Table 8.

TABLE 8

CHP cleavage reaction mixture composition.

| Component | Concentration, wt. %. |
|---|---|
| Phenol | 45.71 |
| Acetone | 36.91 |
| Dicumylperoxide (DCP) | 0.01 |
| Dimethylbenzyl alcohol (DMBA) | 0.08 |
| Cumylphenols | 0.57 |
| AMS dimers | 0.29 |
| Acetophenone | 0.70 |
| α-methylstyrene (AMS) | 2.85 |
| Cumene | 11.48 |
| Hydroxyacetone (HA) | 0.12 |
| Mesityl oxide | 0.01 |
| Unknowns | 0.33 |
| Water | 0.96 |

The Examples and Tables show that when the catalyst is only concentrated sulfuric acid instead of a mixture of sulfuric acid and phenol, the amount of impurities is higher, as compared to the Examples where the catalyst was a mixture of sulfuric acid and phenol. As shown by the results in the Tables, the level of hydroxyacetone is significantly higher in Example 6 than in Examples 2 to 5. Additionally, the level of unknowns and tar is much higher in Example 6 than in Examples 1 to 5.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims. One skilled in the art would recognize that in a reaction conducted using a feedstock of a different composition than the starting composition used in the experiments, the results may differ from those given in the Examples of the present invention, but the positive effect of using this invention would be retained. For example, if a different feedstock was used that had a lower weight percent CHP as a starting material, the composition mass after the reactor may be different, but it would still improve in the same manner. The effect described in the invention (the production of phenol and acetone using the method and catalyst system of the invention) is not attributed to the specific or particular feed composition. The CHP cleavage feed is technology realization dependent. Concentration variations can be significant. In other words, the observed effect is not CHP synthesis technology and cleavage feed preparation technology dependent.

We claim:

1. A method for the production of phenol and acetone from a cumene hydroperoxide mixture comprising: a first stage and a second stage and at least two serially connected reactors, wherein the first stage comprises decomposition of a cumene hydroperoxide mixture in the presence of a catalyst mixture to form a dicumyl peroxide mixture, and the second stage comprises formation of a phenol and acetone mixture from decomposition of the dicumyl peroxide mixture formed in the first stage, wherein the first stage further comprises:
   a) forming a catalyst mixture by combining sulfuric acid and phenol in a weight ratio of from 2:1 to 1:1000 in a catalyst formation reactor;
   b) holding the catalyst mixture in the catalyst formation reactor at a temperature of about 20 to 80° C. for about 1 to 600 minutes; and,
   c) adding the catalyst mixture to the cumene hydroperoxide mixture to form the phenol and acetone mixture.

2. The method of claim 1, wherein the sulfuric acid is an aqueous sulfuric acid solution comprising at least 75 wt. % sulfuric acid.

3. The method of claim 1, wherein the sulfuric acid is fuming sulfuric acid (oleum).

4. The method of claim 1, wherein water is added in the second stage in an amount of up to 1% of the reaction mass.

5. The method of claim 1, wherein the reaction temperature of the first stage is between 40 and 75° C., and wherein the reaction temperature of the second stage is between 90 and 140° C.

6. The method of claim 1, wherein the sulfuric acid to phenol ratio is from 1:1 to 1:5.

7. The method of claim 1, wherein the catalyst mixture in step b) is held at a temperature of from about 35 to 45° C.

8. The method of claim 1, wherein the reaction time in step b) is from about 60 to about 300 minutes.

9. The method of claim 1, wherein the first stage cleavage temperature is from about 40 to 70° C. and the second stage cleavage temperature is from about 110 to 135° C.

10. The method of claim 1, wherein the sulfuric acid has a concentration of at least 90% sulfuric acid.

11. The method of claim 1, wherein the phenol and acetone mixture formed has a reduced level of hydroxyacetone as compared to a phenol and acetone mixture formed using a catalyst that is only sulfuric acid.

12. A method for the production of phenol and acetone from a cumene hydroperoxide mixture comprising: a first stage and a second stage and at least two serially connected reactors, wherein the first stage comprises decomposition of a cumene hydroperoxide mixture in the presence of a catalyst mixture to form a dicumyl peroxide mixture, and the second stage comprises formation of a phenol and acetone mixture from decomposition of the dicumyl peroxide mixture formed in the first stage, wherein the first stage further comprises:
   a) forming a catalyst mixture by combining sulfuric acid and phenol in a weight ratio of from 2:1 to 1:1000 in a catalyst formation reactor, wherein the sulfuric acid is an aqueous sulfuric acid solution comprising at least 75 wt. % sulfuric acid;
   b) holding the catalyst mixture in the catalyst formation reactor at a temperature of about 20 to 80° C. for about 1 to 600 minutes; and
   c) adding the catalyst mixture to the cumene hydroperoxide mixture to form the phenol and acetone mixture.

13. The method of claim 12, wherein the sulfuric acid is fuming sulfuric acid (oleum).

14. The method of claim 12, wherein the catalyst mixture in step b) is held at a temperature of from about 35 to 45° C.

15. The method of claim 12, wherein the reaction time in step b) is from about 60 to about 300 minutes.

16. The method of claim 12, wherein the phenol and acetone mixture formed has a reduced level of hydroxyacetone as compared to a phenol and acetone mixture formed using a catalyst that is only sulfuric acid.

17. A method for the production of phenol and acetone from a cumene hydroperoxide mixture comprising: a first stage and a second stage and at least two serially connected reactors, wherein the first stage comprises decomposition of a cumene hydroperoxide mixture in the presence of a catalyst mixture to form a dicumyl peroxide mixture, and the second stage comprises formation of a phenol and acetone mixture from decomposition of the dicumyl peroxide mixture formed in the first stage, wherein the first stage further comprises:
   a) forming the catalyst mixture in a catalyst formation reactor by combining sulfuric acid and phenol in a weight ratio of from 2:1 to 1:1000, wherein the sulfuric acid is an aqueous sulfuric acid solution comprising at least 75 wt. % sulfuric acid;
   b) holding the catalyst mixture in the catalyst formation reactor at a temperature of about 35 to 45° C. for about 60 to 300 minutes; and
   c) adding the catalyst mixture to the cumene hydroperoxide mixture to form the phenol and acetone mixture,
   wherein the phenol and acetone mixture formed has a reduced level of hydroxyacetone as compared to a phenol and acetone mixture formed using a catalyst that is only sulfuric acid.

18. The method of claim 17, wherein the sulfuric acid is fuming sulfuric acid (oleum).

19. The method of claim 17, wherein the first stage cleavage temperature is from about 40 to 70° C. and the second stage cleavage temperature is from about 110 to 135° C.

* * * * *